United States Patent [19]
Dillon

[11] Patent Number: 4,581,226
[45] Date of Patent: Apr. 8, 1986

[54] METHOD OF TREATING SENSITIVE ANIMAL TISSUE WITH A SPECIALLY PROCESSED SEAWATER SOLUTION

[76] Inventor: Richard S. Dillon, 150 Mill Creek Rd., Ardmore, Pa. 19003

[21] Appl. No.: 738,535

[22] Filed: May 24, 1985

Related U.S. Application Data

[63] Continuation-in-part of Ser. No. 482,916, Apr. 7, 1983, abandoned.

[51] Int. Cl.$^4$ .............................................. A61K 33/14
[52] U.S. Cl. ..................... 424/49; 424/153; 514/886; 514/887; 514/901; 514/915; 514/928; 514/3; 514/12; 514/21; 514/178; 514/179
[58] Field of Search ................. 424/153, 49; 514/886, 514/887, 901, 915, 928, 3, 12, 21, 178, 179

[56] References Cited

U.S. PATENT DOCUMENTS

| | | | |
|---|---|---|---|
| 40,297 | 10/1863 | Wakefield | 424/153 |
| 42,311 | 4/1864 | Rose | 424/153 |
| 43,866 | 8/1864 | Ragsdale | 424/153 |
| 46,494 | 2/1865 | Pike . | |
| 374,125 | 11/1887 | Kingzett | 424/153 |
| 711,263 | 10/1902 | Robertson . | |
| 923,999 | 6/1909 | Riggs | 424/153 |
| 1,035,536 | 8/1912 | Connery . | |
| 1,465,530 | 8/1923 | Smith | 424/153 |
| 1,471,987 | 10/1923 | Vogt | 424/153 |
| 1,551,638 | 9/1925 | Brady . | |
| 1,554,027 | 9/1925 | Potratz | 424/153 |
| 1,588,288 | 6/1926 | Wright . | |
| 2,547,653 | 4/1951 | Minnis et al. | 424/153 |
| 2,658,851 | 11/1953 | Brandenberger et al. | 424/49 |
| 3,689,636 | 9/1972 | Svajda | 424/49 |
| 3,843,782 | 10/1974 | Krezanoski et al. | 424/153 |
| 4,009,259 | 2/1977 | Ament et al. | 424/153 |
| 4,333,922 | 6/1982 | Herschler | 424/153 |
| 4,371,522 | 2/1983 | Gilbard | 424/153 |

FOREIGN PATENT DOCUMENTS

| | | | |
|---|---|---|---|
| 4037126 | of 1927 | Australia | 424/153 |
| 2646931 | 4/1978 | Fed. Rep. of Germany | 424/153 |
| 450431 | 3/1913 | France | 424/153 |
| 7937M | 5/1970 | France | 424/153 |
| 1596818 | 7/1970 | France | 424/153 |
| 2387654 | 12/1978 | France | 424/153 |
| 2406448 | 6/1979 | France | 424/153 |
| 2484836 | 12/1981 | France | 424/153 |
| 1411432 | 10/1979 | United Kingdom | 424/153 |
| 2064320 | 6/1981 | United Kingdom | 424/153 |
| 519195 | 8/1976 | U.S.S.R. | 424/153 |
| 577030 | 11/1977 | U.S.S.R. | 424/153 |
| 594942 | 3/1978 | U.S.S.R. | 424/153 |
| 643429 | 1/1979 | U.S.S.R. | 424/153 |

OTHER PUBLICATIONS

Shellfish Growing Water Classification Charts, 1982, New Jersey Department of Environmental Protection.
New York Bight Water Quality Summer of 1983, EPA Region II, New York/New Jersey/Puerto Rico/Virgin Islands, U.S.
Environmental Protection Agency, Region II—Surveillance and Monitoring Branch, Edison, N.J. 08837.

*Primary Examiner*—Shep K. Rose
*Attorney, Agent, or Firm*—Dann, Dorfman, Herrell and Skillman

[57] ABSTRACT

A method of treating various sensitive animal body tissues comprising applying to the tissue a solution prepared from specially processed seawater. The solution is prepared by filtering off-shore seawater to remove debris in small organisms, sterilizing the filtered solution and diluting thereafter with tap water or distilled water to lower the solution's osmolality to about 280 mOs, which renders the solution compatible and isotonic with the tissue to be treated.

20 Claims, No Drawings

METHOD OF TREATING SENSITIVE ANIMAL TISSUE WITH A SPECIALLY PROCESSED SEAWATER SOLUTION

RELATED APPLICATION

The present invention is a continuation-in-part of prior co-pending application Ser. No. 482,916 filed Apr. 7, 1983, and now abandoned.

FIELD OF THE INVENTION

The present invention relates to a composition of matter obtained by specially processing seawater and particularly to the use of such composition in cleansing and healing animal body tissue.

BACKGROUND OF THE INVENTION

Folklore attributes to seawater a variety of healing powers. It is possible that the high salt concentration and resulting high osmolality of seawater contributes to whatever healing power seawater might have. Medical science has yet to confirm or refute healing powers attributable to seawater.

Many prior art methods have been proposed for the treatment of various animal body tissues with solutions containing sodium chloride and other ingredients. One such method involves treating skin and scalp conditions with a saline solution. The solution is prepared by evaporating seawater by heat, subjecting the concentrated liquid obtained to a low temperature to separate by crystallization a part of the magnesium sulphate and a part of the sodium and potassium chlorides, drawing off the liquor from the precipitate, redissolving the magnesium sulphate and adding the liquor with a small amount of acetic acid to the solution. Another method involves forming a saline solution by dissolving zinc sulphate and sodium chloride in water and applying it as an eyewash or lotion. Still another method relates to the use of salts of an alkali-forming metal containing small amounts of available chlorine and even smaller amounts of free alkali as a germicidal solution.

There are currently on the market several pharmaceutical products which mimic the hyperosmolar effect of seawater. A product sold under the name of Debrisan acts as a hypertonic solution; it consists essentially of hydrophilic beads of dextranomer, which, it is claimed, sucks fluid and bacteria out of wounds. The small beads are poured directly onto the wound, and, of course, must be washed out periodically.

There are, however, various disadvantages associated with application of seawater and other similar hypertonic solutions to sensitive and/or inflamed tissue. Hypertonic solutions shrink normal tissue, and will, for example, irritate mucosal tissue such as that found in the eye, nose, throat, vagina, etc. Hypertonic solutions are also known to desensitize a variety of bacteria that might otherwise be susceptible to antibiotic therapy. Many antibiotics are effective in that they damage bacterial membranes thus inhibiting reproduction of the bacteria. Hypertonic solutions may serve to stabilize bacterial membranes, thus blunting the effect of such antibiotics.

SUMMARY OF THE INVENTION

The above-noted disadvantages associated with prior art methods in which hypertonic solutions are used to treat various animal body tissues have been overcome in accordance with present invention wherein various sensitive tissues are treated by applying to the tissue a solution prepared from a specially processed seawater. The solution is obtained by filtering off-shore seawater for example water off the New Jersey shore which is not condemned or prohibited for the harvest of oysters, clams and mussels as identified in "State of New Jersey Shellfish Growing Water Classification Charts" published 1982 by New Jersey Department of Environmental Protection. The water is filtered to remove debris and small organisms, then diluted the seawater with tap water or distilled water to lower its osmolality to about 280 mOs (compatible and isotonic with human serum), and the resulting solution is boiled or otherwise sterilized to sterilize the same to provide a sterilized solution with osmolality isotonically compatible with the tissue treated. Alternatively, the solution may be sterilized first and then diluted with sterile water to provide the aforesaid osmolality.

Seawater processed in this manner is particularly useful as a treating solution for sensitive body tissue. For example, the treating solution may be used for irrigating irritated skin and mucosal surfaces such as the nose, ear, throat, eye, vagina, etc. In addition, the present invention is especially effective as a wound soak, particularly since, it is believed that the solution inhibits the growth of some pathogens such as staphylococcus aureus.

Preparation of the treating solution used in carrying out the method of the present invention is relatively inexpensive. No specialized equipment is required in preparing the solution or in applying it to various sensitive tissues. These factors are significant from the standpoint of application of the invention on a commercial scale.

Aside from providing a practical, economic and effective solution for treating sensitive tissue, the treating solution of the present invention also has the advantage that it is diluted to an osmolality of about 280 mOs, which is isotonic with human serum and tissue and, therefore, soothes rather than irritates sensitive tissue. Furthermore, the isotonic solution of the present invention does not interfere with the therapeutic effect of antibiotics since it does not stabilize bacterial membrane.

In addition to the utilities noted above, the specially processed seawater of the present invention also has application as a culture media for bacteria such as pseudomonas, which bacteria are acclimated to saline environments. The solution may also be used as an electrolyte media for tissue cultures if appropriate amino acids and substrate are added.

DETAILED DESCRIPTION OF THE INVENTION

The seawater employed in the present invention preferably is obtained at sites where there is little risk of contamination. Removal of debris and small organisms may be achieved by filtering the off-shore seawater through a fine grade laboratory filter paper, although larger commerical filters may be used. The filtered water may then be sterilized by boiling it over a burner for a time sufficient to achieve sterilization of the solution. The concentration of sea salts in the resulting solution is dependent on the length of time it is boiled. Ultraviolet light or other techniques may also be used as long as the product is shown to be sterile. Finally, the sterilized filtered solution is diluted with distilled or tap water to an osmolality compatible with animal tissue, which generally ranges from about 275 mOs to about 295 mOs. The amount of sterile water added is selected to dilute the resulting solution to the desired osmolality.

The specially prepared solution of the present invention may be used as a wound soak in the treatment of irritated epidermal, ulcerated (including burned tissue) and inflamed tissues, and as an irrigating solution for sensitive mucosal tissue.

When used as a wound soak, a bactericide or bacteriostatic agent may be added to the solution in an amount sufficient to control bacterial growth. For instance, Betadine or an antibiotic could be added to the solution to render it bactericidal. In certain instances, however, the solution itself has exhibited bacteriostatic properties. In particular, it has been found that the specially processed solution of the present invention inhibits the growth of common skin pathogens such as staphylococcus aureus. It is believed the inherent bacteriostatic property of the solution is due to growth inhibiting amounts of magnesium, calcium and chloride present therein. Thus, the solution may, in certain circumstances be used to treat inflamed tissue by applying the solution as a bacteriostatic emollient.

Anabolic hormones such as thyroxine, insulin, growth hormone, testosterone and nandrolone may also be added to the specially processed solution in amounts sufficient to stimulate the multiplication of tissue cells being treated when the solution is being used as a wound soak. Low concentrations of other hormones such as cortisol may also be added in order to promote multiplication of tissue cells.

The solution may also be used to treat various irritated mucosal tissue, since the solution is isotonically compatible with tissue, and as such would soothe and comfort irritated tissue. For example, the solution may be used to irrigate eye and nasal mucosa, pharyngeal mucosa, external auditory meatus, tissue lining the cavity of the mouth and vaginal tissue. Thus, when used for irrigation, the solution may be applied as a nose spray, an ear and eyewash, a mouth wash and also as a douche.

Mucosal surfaces equipped with ciliated cells may be especially benefitted by treatment with the solution of the present invention. Various studies have shown that cilia in many metazoa stop beating when bathed in calcium-free and/or magnesium-free solutions such as saline. The common practice of using saline sprays for the respiratory tract and in vaginal douches may therefore be potentially harmful since it may interfere with or inhibit the beating of cilia on ciliated mucosal surfaces. The solution of the present invention, containing therein both calcium and magnesium, would not exhibit this adverse effect on ciliated mucosal surfaces.

As noted above, in addition to its utility as a wound soak and irrigating solution, the specially processed seawater of the present invention may be used to culture certain bacteria, particularly those which are acclimated to saline environments. One such strain of bacteria, pseudomonas, shows significant growth in the specially prepared solution. Pseudomonas is used commercially to reduce oil spills in the ocean.

The solution may also, as mentioned above, be used to culture cells from animal tissue since the solution is isotonically compatible with said tissue. As known to those skilled in the art, it is necessary when culturing animal tissue cells, to add to the solution appropriate amounts of amino acids and substrate (i.e., glucose). Optional amounts of growth hormone, thyroxine, testosterone, estrogen, or other anabolic hormones and factors such as epidermal growth hormone and vitamins may also be added to promote growth of cells when using the solution as a culture media.

Finally, since the solution of the present invention has been shown to soothe rather than irritate sensitive animal tissue, it may, in addition to the above-mentioned uses, be used as a vehicle for the addition of bactericides, antibiotics and the like, particularly when it has been determined that the patient has a bacterial infection that might otherwise prosper in such a medium. In such a case, the patient derives benefit from application of the solution to the infected area since it serves to soothe and heal irritated and inflamed tissue, and also receives the benefit of the prescribed antibiotic therapy.

The following examples further describe the manner and process of making and using the invention and sets forth the best mode contemplated for carrying out the invention, but are not to be construed as limiting the invention. Example 1 is a typical procedure for making the specially processed solution of the present invention.

EXAMPLE 1

500 cc of seawater was obtained at a site off the New Jersey shore. The 500 cc sample was filtered through a standard filtering device using a Whatman No. 2 filter paper. The sample was then sterilized by boiling the solution over a Bunsen burner for one (1) minute. The filtered sterilized sample was used as a stock material, and, when used for its intended purpose, was diluted with distilled water at a ratio of 2.2 parts distilled water to one (1) part filtered sterilized seawater to achieve an osmolality of 280 mOs.

Examples 2–4 set forth the results of clinical applications and observations of a specially processed solution prepared as per Example 1 in treating sensitive tissue of patients with diabetes. Diabetics generally experience difficulties in regeneration of tissue due to the vascular complications of their disease.

EXAMPLE 2

M. F., an eighty-one year old diabetic female, had a serious contusion on the instep of her right foot. Warm soaks of plain water were applied for about two weeks to no effect, since at the end of the two weeks the foot was swollen with a black area the size of a 50 cent piece on the lateral instep. A golfball-sized hematoma was expressed leaving a large defect in her swollen foot. Thereafter, for three weeks, the swollen area was irrigated with a saline solution and covered with a saline-soaked gauze between the irrigations. The contusion had good granulation tissue in its base but the surrounding skin was not moving across the epithelial surface. The patient was then provided with the specially processed solution of the present invention which was poured on gauze on top of the contusion. The soaked gauze was covered with an air-impermeable plastic film, i.e. Saran Wrap ®, to prevent the gauze from drying out. Every few hours a freshly soaked gauze was applied. At night the gauze was allowed to dry out. The contusion immediately appeared to decrease in size as the epithelial cells moved from the edges of the contusion across the defect. New skin matured and five weeks after the introduction of the specially processed solution of the present invention, the foot appeared normal.

EXAMPLE 3

M. G., a fifty-five year old diabetic female, underwent a femoropopliteal bypass and then a transmetatarsal amputation of her right foot because of gangrene of her right fifth toe. Postoperatively the flaps of skin over the amputation necrosed and the patient underwent compression boot therapy to improve the arterial circulation to her foot. The necrosed areas slowly healed except for a defect the size of a 25 cent piece lateral and above the distal first metatarsal segment. Several months after the amputation, the patient was again hospitalized for an attempted skin graft, which failed. Treatment with the specially processed solution of the present invention was then begun. The wound area was covered with gauze wetted with the specially processed solution, and again covered with an air-impermeable plastic film, i.e. Saran Wrap ®. The wet gauze was changed every few hours during the day and again allowed to dry at night. The defect epithelized over from the edges and healed.

EXAMPLE 4

F. F., a sixty-three year old diabetic male with multiple myeloma, developed a 7 cm. ulcer on the dorsum of his right foot along with smaller ulcers on each of his toes and over his internal malleolus while in the postoperative period after his left leg was amputated above the knee. He received compression boot therapy to his remaining leg over a year, healing all but the large ulcer on the dorsum of his foot. He was again hospitalized for skin grafting which was delayed because he fell out of bed and broke his hip. Thereafter, the ulcer was treated with the specially processed solution of the present invention. The specially processed solution was poured on gauze dressings which were changed every few hours during the day. Two days after treatment had begun a "scum" appeared to be covering the wound from its edges. This proved to be epithelial tissue which covered all but a few millimeters of his ulcer after 8 days of treatment.

In the above-described Examples, the soaked gauze dressings were frequently changed to avoid promoting growth of bacteria that might have been resistant to the growth retarding effect of magnesium, calcium and chloride present in the solution.

In these and other cases, application of the specially processed solution appears to promote the healing of damaged tissue that was unresponsive to other forms of therapy. That is, the solution provides a media that promotes epithelial cell growth.

As mentioned above, the specially processed solution of the present invention may be used to irrigate sensitive or irritated mucosal tissue. For instance, the solution may be used as a nasal lavage to irrigate the nasal mucosa to remove discomforting secretions which block the sinuses and/or eustachian tube. The solution may also be used as an eyewash when the eye is infected or has discomfort-causing particulate matter therein. In addition, women may routinely use the prepared solution as a douche. In particular, women with severe vaginitis may benefit from the use of this solution.

Finally, as mentioned above, the specially processed solution of the present invention may be used as a culture medium. Pseudomonas shows significant growth when cultured in a media containing the specially processed solution of the present invention. In particular, when cultured at room temperature for three hours, pseudemonas shows more growth in a media containing the specially processed solution than in laboratory broth or saline.

I claim:

1. The method of treating sensitive animal tissue which comprises applying to said tissue an aqueous solution prepared by processing seawater to separate debris and small organisms therefrom, sterilizing and diluting the resulting solution to provide a sterilized solution with osmolality isotonically compatible with said animal tissue.

2. The method of claim 1, wherein said tissue comprises irritated epidermal tissue, and said treatment comprises irrigating said irritated tissue with said solution.

3. The method of claim 1, wherein said tissue comprises ulcerated tissue, and said treatment comprises applying said sterilized solution as a wound soak.

4. The method of claim 3, comprising adding to said sterilized solution an amount of an agent sufficient to control bacterial growth.

5. The method of claim 4, wherein said agent is a bacteriostatic agent.

6. The method of claim 4, wherein said agent is a bactericidal agent.

7. The method of claim 3, comprising adding to said sterilized solution an amount of anabolic hormone sufficient to stimulate multiplication of tissue cells.

8. The method of claim 7, wherein said anabolic hormone is selected from the group of thyroxine, insulin, growth hormone, testosterone and nandrolone.

9. The method of claim 3, comprising adding to said solution an amount of cortisol sufficient to promote multiplication of tissue cells.

10. The method of claim 1, wherein said tissue comprises inflamed tissue, and said treatment comprises applying said sterilized solution as a bacteriostatic emollient.

11. The method of claim 1, wherein said tissue comprises a mucosal surface, and said treatment comprises irrigating said mucosal surface with said solution.

12. The method of claim 11, wherein said mucosal surface is equipped with cilia.

13. The method of claim 11, wherein said mucosal surface comprises nasal membrane.

14. The method of claim 11, wherein said mucosal surface comprises pharyngeal tissue.

15. The method of claim 11, wherein said mucosal surface comprises the external auditory meatus.

16. The method of claim 11, wherein said mucosal surface comprises tissue lining the cavity of the mouth, and said treatment comprises applying said solution as a mouthwash.

17. The method of claim 11, wherein said mucosal surface comprises eye tissue, and said treatment comprises applying said solution as an eyewash.

18. The method of claim 11, wherein said mucosal surface is vaginal tissue, and said treatment comprises applying said solution as a douche.

19. The method of claim 1, wherein said sterilization is performed prior to dilution, and said dilution is performed with distilled water.

20. The method of claim 19, wherein said sterilization is performed by boiling said resulting solution for a time sufficient to render said solution sterile.

* * * * *